United States Patent
Mansbridge et al.

(10) Patent No.: US 6,291,240 B1
(45) Date of Patent: Sep. 18, 2001

(54) CELLS OR TISSUES WITH INCREASED PROTEIN FACTORS AND METHODS OF MAKING AND USING SAME

(75) Inventors: Jonathan N. Mansbridge, La Jolla; Kang Liu, San Diego, both of CA (US)

(73) Assignee: Advanced Tissue Sciences, Inc., La Jolla, CA (US)

( * ) Notice: Subject to any disclaimer, the term of this patent is extended or adjusted under 35 U.S.C. 154(b) by 0 days.

(21) Appl. No.: 09/137,567

(22) Filed: Aug. 21, 1998

Related U.S. Application Data (60) Provisional application No. 60/072,945, filed on Jan. 29, 1998.

(51) Int. Cl.$^7$ .............................. C12N 5/00; C12N 5/06; C12N 5/10
(52) U.S. Cl. .......................... 435/395; 435/1.3; 435/325; 435/347; 435/373; 435/402; 435/455
(58) Field of Search ............................ 435/1.3, 325, 347, 435/375, 395, 402, 455, 240.23, 373; 536/23.1, 23.5, 24.1

(56) References Cited

U.S. PATENT DOCUMENTS

| | | | |
|---|---|---|---|
| 4,963,489 | 10/1990 | Naughton | 435/240.1 |
| 5,145,770 | * 9/1992 | Tubo et al. | 435/1 |
| 5,447,843 | * 9/1995 | McGuire et al. | 435/6 |
| 5,460,939 | 10/1995 | Hansbrough et al. | 435/1.1 |
| 5,478,739 | * 12/1995 | Slivka | 435/240.23 |
| 5,891,617 | * 4/1999 | Watson et al. | 435/1.3 |
| 5,902,741 | * 5/1999 | Purchio et al. | 435/240.23 |

FOREIGN PATENT DOCUMENTS

| | | |
|---|---|---|
| 0 358 506 | 3/1990 | (EP) . |
| WO 97/24144 | 7/1997 | (WO) . |

OTHER PUBLICATIONS

Kim et al., J. Biol. Chem., 264:402–408, 1989.*
Lafyatis et al., J. Biol. Chem., 265:19128–19136, 1990.*
Liu et al., J. Biol. Chem., 271:26281–26290, 1996.*
Finch et al., J. Biol. Chem., 270:11230–11237, 1995.*
Shima et al., J. Biol. Chem., 271:3877–3883, 1989.*
H.R. Maurer, in Animal Cell Culture, A Practical Approach, IRL Press, Washington D.C., Ed., R.I. Freshney, Chapter 2, pp. 23, 29, and 30, 1989.*
Detmar et al., 1997, "Hypoxia Regulates the Expression of Vascular Permeabilty Factor/Vascular Endothelial Growth Factor (VPF/VEGF) and Its Receptors in Human Skin", J. Invest. Dermatol. 108:263–268.
Mhiri et al., 1997, "The Promoter of the Tobacco Tnt1 Retrotransposon is Induced by Wounding and by Abiotic Stress", Plant Mol. Biol. 33:257–266.
Neeman et al., 1997, "Regulation of Angiogenesis by Hypoxic Stress: From Solid Tumours to the Ovarian Follicle", Int. J. Exp. Path. 78:57–70.
Storey et al., 1997, "De Novo Protein Biosynthesis Responses to Water Stress in Wood Frogs: Freeze–Thaw and Dehydration–Rehydration", Cryobiol. 34:200–213.
Yang and De Bono, 1997, "A New Role for Vascular Endothelial Growth Factor and Fibroblast Growth Factors: Increasing Endothelial Resistance to Oxidative Stress", FEBS Lett. 403:139–142.
Gonzales–Rubio et al., 1996, "Oxidative Stress Induces Tyrosine Phosphorylation of PDGF α–and β–Receptors and pp60$^{c-src}$ in Mesangial Cells", Kidney Intl. 50:164–173.
Imai et al., 1996, "A Lea–Class Gene of Tomato Confers Salt and Freezing Tolerance when Expressed in *Saccharomyces cerevisiae*", Gene 170:243–248.
Kaye and Guy, 1995, "Perspective of Plant Cold Tolerance: Physiology and Molecular Reponses", Science Progress 78:271–299.
Lewis et al., 1995, "Induction of Heat, Freezing and Salt Tolerance by Heat and Salt Shock in *Saccharomyces cerevisiae*", Microbiol. 141:687–694.
Stein et al., 1995, "Stabilization of Vascular Endothelial Growth Factor mRNA by Hypoxia and Hypoglycemia and Coregulation with Other Ischemia–Induced Genes", Mol. Cell. Biol. 15:5363–5368.
Yao et al., 1995, "Cryogenic Spinal Cord Injury Induces Astrocytic Gene Expression of Insulin–Like Growth Factor I and Insulin–Like Growth Factor Binding Protein 2 During Myelin Regeneration", J. Neurosci. Res. 40:647–659.
Molecular Biology and Biotechnology, A Comprehensive Desk Reference, 1995, R. Myers, ed., VCH Publishers, Inc., pp. 200–202.
Goldberg et al., 1991, "Erythropoietin mRNA Levels Are Governed by Both the Rate of Gene Transcription and Posttranscriptional Events", Blood 77:271–277.
Goldberg et al., 1988, "Regulation of the Erythropoietin Gene: Evidence That the Oxygen Sensor is a Heme Protein", Science 242:1412–1414.

* cited by examiner

Primary Examiner—Deborah J. R. Clark
Assistant Examiner—Janet M. Kerr
(74) Attorney, Agent, or Firm—Pennie & Edmonds LLP (57) ABSTRACT

The invention relates to cells or tissues having an increased amount of regulatory proteins, including cytokines, growth factors, angiogenic factors and/or stress proteins, and methods of producing and using those cells or tissues. The invention is based on the discovery that the production of regulatory proteins is induced in cells or tissue constructs following cryopreservation and subsequent thawing of the cells or constructs. The compositions and methods of this invention are useful for the treatment of wound healing and the repair and/or regeneration of other tissue defects including those of skin, cartilage, bone, and vascular tissue as well as for enhancing the culture and/or differentiation of cells and tissues in vitro.

21 Claims, 5 Drawing Sheets

CELLS OR TISSUES WITH INCREASED PROTEIN FACTORS AND METHODS OF MAKING AND USING SAME

The present application claims the benefit under 35 U.S.C. §119(e) of copending provisional application Ser. No. 60/072,945, filed on Jan. 29, 1998, which is incorporated herein by reference in its entirety.

INTRODUCTION

The invention relates to cells or tissues having an increased amount of at least one regulatory protein, and methods of producing and using those cells or tissues. More specifically, the invention relates to the induced production of regulatory proteins, such as cytokines, growth factors, angiogenic factors, inflammatory mediators and/or stress proteins, in cells or tissue constructs following cryopreservation and subsequent thawing of the cells or tissues. The compositions and methods of this invention are useful for the treatment of wound healing and the repair and/or regeneration of other tissue defects including those of skin, cartilage, bone, neurons, astrocytes, and vascular tissue as well as for enhancing the culture and/or differentiation of cells and tissues in vitro.

1. BACKGROUND

The ability to induce regulatory proteins such as growth factors, cytokines, and stress proteins in cells or tissues opens new possibilities in the preparation of tissue-engineered products for use in tissue repair, e.g., in the treatment of wounds and other tissue defects. For example, growth factors are known to play an important role in the wound healing process and evidence indicates that some stress proteins may also be important in this process. In general, it is thought desirable in the treatment of wounds to enhance the supply of growth factors by direct addition or, in the case of tissue-engineering, by enhancing cellular production.

Cellular cytokines and growth factors are involved in a number of critical cellular processes including cell proliferation, adhesion, morphologic appearance, differentiation, migration, inflammatory responses, angiogenesis, and cell death. Many of these cytokines and factors are induced as a result of stress placed upon cells. For example, studies have demonstrated that hypoxic stress and injury to cells induce responses including increased levels of mRNA and proteins corresponding to growth factors such as PDGF (platelet-derived growth factor), VEGF (vascular endothelial growth factor), FGF (fibroblast growth factor), and IGF (insulin-like growth factor) (Gonzalez-Rubio, M. et al., 1996, Kidney Int. 50(1):164–73; Abramovitch, R. et al., 1997, Int J. Exp. Pathol. 78(2):57–70; Stein, I. et al., 1995, Mol Cell Biol. 15(10):5363–8; Yang, W. et al., 1997, FEBS Lett. 403(2):139–42; West, N. R. et al., 1995, J. Neurosci. Res. 40(5):647–59). Many of these responses include a cascade type reaction via tyrosine phosphorylation or the induction of stress proteins.

Two known stress proteins are GRP78 and HSP90. These proteins stabilize cellular structures and render the cells resistant to adverse conditions. Some stress proteins have also been found to aid in wound healing through the induction of growth factors, such as transforming growth factor-β, also known in the art as TGF-β. This family of dimeric proteins includes TGF-β1, TGF-β2, and TGF-β3 and regulates the growth and differentiation of many cell types. Furthermore, this family of proteins exhibits a range of biological effects, stimulating the growth of some cell types (Noda et al., 1989, Endocrinology 124:2991–2995) and inhibiting the growth of other cell types (Goey et al., 1989, J. Immunol. 143:877–880; Pietenpol et al., 1990, Proc. Natl. Acad. Sci. USA 87:3758–37662). TGF-β has also been shown to increase the expression of extracellular matrix proteins including collagen and fibronectin (Ignotz et al., 1986, J. Biol. Chem. 261:4337–4345) and to accelerate the healing of wounds (Mustoe et al., 1987, Science 237:1333–1335).

Another such growth factor is PDGF. PDGF was originally found to be a potent mitogen for mesenchymal-derived cells (Ross R. et al., 1974, Proc. Natl. Acad. Sci. USA 71(4):1207–1210; Kohler N. et al., 1974, Exp. Cell Res. 87:297–301). Further studies have shown that PDGF increases the rate of cellularity and granulation in tissue formation. Wounds treated with PDGF have the appearance of an early stage inflammatory response including an increase in neutrophils and macrophage cell types at the wound site. These wounds also show enhanced fibroblast function (Pierce, G. F. et al., 1988, J. Exp. Med. 167:974–987). Both PDGF and TGF-β have been shown to increase collagen formation, DNA content, and protein levels in animal studies (Grotendorst, G. R. et al., 1985, J. Clin. Invest. 76:2323–2329; Sporn, M. B. et al., 1983, Science (Wash D.C.) 219:1329). The effect of PDGF in wound healing has been shown to be effective in human wounds. In human wounds, PDGF-AA expression is increased within pressure ulcers undergoing healing. The increase of PDGF-AA corresponds to an increase in activated fibroblasts, extracellular matrix deposition, and active vascularization of the wound. Furthermore, such an increase in PDGF-AA is not seen in chronic non-healing wounds (Principles of Tissue Engineering, R. Lanza et al. (eds.), pp. 133–141 (R.G. Landes Co. TX 1997). A number of other growth factors having the ability to induce angiogenesis and wound healing include VEGF, KGF and basic FGF.

A number of attempts have been made at increasing wound healing through the use of topical gels, ointments, and lotions containing angiogenic or other growth factors. These attempts have incorporated various growth factors and cytokines or combinations thereof. Some success has been recognized; however, problems exist with regard to the quantities, application, and responsiveness to these ointments. Such problems include the need for recurrent applications over a period of time, varying concentrations or application times, and adverse reactions to exogenous factors.

There are currently no simple effective methods or compositions for application of cytokines, growth factors or other regulatory proteins for the repair and regeneration of tissue defects, whereby the amount and duration of such proteins is determined by a naturally-occurring physiological response.

2. SUMMARY OF THE INVENTION

The present invention relates to cells or tissues containing an increased amount of at least one regulatory protein, and methods of producing and using those cells or tissues. More specifically, the present invention relates to the induction of regulatory proteins such as cytokines, growth factors, angiogenic factors, inflammatory mediators and/or stress proteins, in cells or tissues by cryopreservation of the cells or tissues, followed by thawing. The cryopreservation/thaw cycle induces the expression in the cells or tissues of one or more genes that encodes a regulatory protein such as a cytokine, growth factor, angiogenic factor, inflammatory mediator and/or stress protein, thus providing the cells or tissues with an increased amount of one or more of these factors.

According to the present invention, the cells or tissues are cryopreserved or frozen to below −50° C.; more preferably, to below −65 to −70° C. However, the cells or tissues may be frozen to temperatures as low as −150 to −180° C. The cryopreserved cells or tissues can be stored for a period of years, although they should be checked periodically for maintenance of viability. In order to induce the production of the regulatory proteins in accordance with this invention, the cryopreserved cells or tissues are thawed rapidly, preferably in a water bath at 34–37° C., to avoid damage to the cells.

According to one embodiment of the invention, cells are grown in two-dimensional culture, e.g., on a monolayer, and subjected to cryopreservation, followed by thawing.

According to another embodiment, cells are grown in three-dimensional culture and subjected to cryopreservation and subsequent thawing. According to a further preferred embodiment, the cells are grown on a non-living three-dimensional support, framework or scaffold to form a tissue construct that is subjected to cryopreservation and subsequent thawing for the enhanced production of regulatory proteins.

Thus, a preferred embodiment of the invention is a tissue construct comprising cells attached to a non-living three-dimensional framework, the tissue construct containing an increased amount of regulatory proteins. According to a further preferred embodiment, the three-dimensional framework is composed of a biodegradable material such as cotton, polyglycolic acid, polycaprolactones, cat gut sutures, cellulose, gelatin or dextran. According to another embodiment, the three-dimensional framework is composed of a non-biodegradable material such as nylon (polyamides), dacron (polyesters), polystyrene, polypropylene, polyacrylates, polyvinyls, polycarbonates, teflons (polytetrafluoroethylenes) or a nitrocellulose compound.

The cells or tissues to be induced according to this invention are preferably mammalian; most preferably, human. Moreover, the cells may be derived from any of a variety of tissues, including epithelial, stromal or parenchymal tissue. In one preferred embodiment, stromal cells are grown on a three-dimensional framework to form a tissue construct, e.g., a stromal matrix, dermal construct or cartilage construct, that is subjected to cryopreservation, followed by thawing for the enhanced production in the tissue construct of regulatory proteins such as growth factors, angiogenic factors, inflammatory mediators and/or stress proteins.

According to one such embodiment, stromal cells are grown on a three-dimensional framework to form a tissue construct comprising a living stromal matrix. As described in further detail infra, the living stromal matrix comprises stromal cells and connective tissue proteins naturally secreted by the stromal cells attached to and substantially enveloping a framework composed of a biocompatible, non-living material formed into a three-dimensional structure. Parenchymal cells from any of a variety of sources, e.g., liver, bone, pancreas, are then inoculated on to the stromal matrix to form a tissue-specific three-dimensional tissue construct, that is subjected to cryopreservation, followed by thawing for the enhanced production in the tissue construct of regulatory proteins such as growth factors, angiogenic factors, inflammatory mediators and/or stress proteins. According to an alternative embodiment, the stromal matrix may be subjected to cryopreservation, followed by thawing prior to inoculation of the parenchymal cells; in this embodiment, the induction of increased amounts of regulatory proteins in the stromal matrix prior to inoculation of the parenchymal cells enhances the growth in culture of the subsequently-inoculated parenchymal cells. According to yet another alternative embodiment, the tissue construct is subjected to physiological stresses such as oxygen deprivation or nutrient deficiency, either prior to or after inoculation of the parenchymal cells. The stress imposed on the stromal matrix and/or parenchymal cells by the oxygen or nutrient deprivation induces the production of regulatory proteins in the matrix and/or cells, which proteins will enhance the growth of the construct.

The compositions and methods of this invention lead to the production of enhanced wound healing products and products for the repair and/or regeneration of damaged tissue. For example, in general, it is thought desirable in the treatment of ulcers to enhance the supply of growth factors to the ulcer. Thus, the induced tissue constructs described herein, i.e., containing increased amounts of, e.g., growth factors and/or angiogenic factors, can be implanted in vivo at the site of a wound or tissue damage, such as an ulcer, to promote the healing and repair of that wound or tissue damage. In addition, the compositions and methods of this invention are useful to promote the in vitro culture and differentiation of cells and tissues.

3. DEFINITIONS

The following terms used herein shall have the meanings indicated:

Adherent Layer: cells attached directly to a two-dimensional monolayer or a three-dimensional framework, or cells connected indirectly by attachment to cells that are themselves attached directly to the monolayer or framework.

Stromal Cells: mesenchymal stem cells, prechondrogenic cells, stem cells, chondrocytes, chondrocyte progenitors, fibroblasts, and fibroblast-like cells (i.e., those having morphologic appearances similar to fibroblasts) with or without other cells and/or elements found in connective tissue, including but not limited to, endothelial cells, pericytes, macrophages, monocytes, plasma cells, mast cells, adipocytes, etc.

Parenchymal Cells: cells which form the essential and distinctive tissue of an organ as distinguished from its supportive structure, also defined herein as tissue-specific cells.

Three-Dimensional Framework or Scaffold: a three-dimensional support composed of any material and/or shape that (a) allows cells to attach to it (or can be modified to allow cells to attach to it); and (b) allows cells to grow in more than one layer. This support is inoculated with stromal cells to form a living stromal matrix. For example, the structure of the framework can include a mesh, a sponge or a hydrogel.

Living Stromal Matrix: a three-dimensional framework which has been inoculated with stromal cells, which cells proliferate on the framework and elaborate regulatory factors and extracellular matrix proteins that are deposited on the framework to form a living stromal tissue. The living stromal matrix will support the growth of tissue-specific cells that can be inoculated onto or into the matrix.

Tissue-Specific Three-Dimensional Construct: a three-dimensional stromal matrix which has been inoculated with tissue-specific or parenchymal cells and cultured. In general, the tissue-specific cells used to inoculate the three-dimensional stromal matrix should include the stem cells or early progenitor cells for that tissue, i.e., those cells which generate new cells that will mature into the specialized cells that form the parenchyma of the tissue.

5. DETAILED DESCRIPTION OF THE INVENTION

The present invention relates to the induced production of one or more regulatory proteins such as cytokines, growth factors, angiogenic factors, inflammatory mediators and/or stress proteins, in cells or tissues, including tissue-engineered constructs. More specifically, the present invention relates to cells and tissues containing increased amounts of one or more of these regulatory proteins and methods of preparing and using the cells or tissues. As used herein, the term "having an increased amount of regulatory proteins" refers to cells or tissues that have elevated levels of mRNA encoding at least one regulatory protein and produce increased amounts of the protein(s) relative to cells or tissues that have not been stressed, e.g., by cryopreservation and subsequent thawing.

The invention is based, in part, on the discovery that regulatory proteins can be induced in cells or tissues by cryopreservation of the cells or tissues, followed by thawing. The cryopreservation/thaw cycle induces the expression in the cells or tissues of at least one gene encoding a regulatory protein such as a cytokine, growth factor, angiogenic factor, inflammatory mediator and/or stress protein, thus providing the cells or tissues with an increased amount of at least one of these factors. The present invention also relates to the use of the cells, tissues and/or tissue constructs for wound healing or the repair or regeneration of tissue damage in vivo. The compositions and methods described herein also find use in enhancing the culture and/or differentiation of cells and tissues in vitro.

As used herein, the term "regulatory protein" refers to any of a number of proteins that are produced by cells and regulate cell or tissue functions; such proteins include but are not limited to cytokines, growth factors, angiogenic factors, inflammatory mediators, and stress proteins. Examples of cytokines and growth factors that may be induced according to the methods of this invention include but are not limited to TGF-β, PDGF, VEGF, KGF, FGFs, HBEGF, HGF, and BMPs (bone morphogenic proteins, e.g., BMP-1 and BMP-2). Examples of angiogenic factors that can be induced according to the methods of this invention include VEGF, KGF, FGFs (e.g., bFGF), HGF, and angiopoietin. Examples of inflammatory mediators that can be induced according to this invention include TGF-$\beta$, PDGF, IL-6, IL-8, and G-CSF. Examples of stress proteins that can be induced according to the methods described herein include GRP78 and HSP90.

As used herein, the term "cryopreservation" relates to the freezing of cells and/or tissues under conditions that maintain the cells' viability upon subsequent thawing. General techniques for cryopreservation of cells are well-known in the art; see, e.g., Doyle et al., (eds.), 1995, *Cell & Tissue Culture: Laboratory Procedures,* John Wiley & Sons, Chichester; and Ho and Wang (eds.), 1991, *Animal Cell Bioreactors,* Butterworth-Heinemann, Boston, which are incorporated herein by reference.

According to the present invention, cells or tissues can be grown on a substrate in either two-dimensional or three-dimensional cultures in vitro and subjected to cryopreservation, followed by thawing. As used herein, the term "substrate" refers to any surface upon which cells can attach and grow. Two-dimensional cell culture can include the culture of cells as a monolayer or on a monolayer substrate in vitro or other two-dimensional cultures such as simple in vitro epithelial cultures. Subjecting such cultures to cryopreservation and thawing according to this invention induces the production in the cultures of increased amounts of regulatory proteins.

According to a preferred embodiment, cells are grown on a non-living three-dimensional framework or scaffold support structure. Preferably, the cells grown on the scaffold are mammalian and more preferably, human stromal cells, as defined supra, which cells are inoculated onto or into the three-dimensional framework and proliferate thereon to form a living stromal matrix. For example, the stromal cells can comprise fibroblasts, chondrocytes, mesenchymal stem cells, with or without additional cells and/or elements as defined supra. According to one embodiment wherein the tissue to be grown is skin, the stromal cells comprise fibroblasts with or without other cells such as endothelial cells, pericytes, plasma cells, mast cells, etc, as defined supra. According to another embodiment wherein the tissue to be grown is cartilage, the stromal cells comprise chondrocytes and/or chondrocyte progenitor cells as well as fibroblasts with or without additional cells as defined supra.

The stromal cells used according to this invention can be fetal or adult in origin, and can be derived from organs such as skin, cartilage, liver, pancreas, etc. Such tissues and/or organs can be obtained by appropriate biopsy or upon autopsy; cadaver organs may be used to provide a generous supply of stromal cells and elements. However, the use of cells from allogeneic sources may result in problems associated with graft rejection due to immunological factors. Thus, in certain cases, it may be preferable to use undifferentiated or fetal stromal cells, e.g., fibroblast-like progenitor cells or mesenchymal stem cells. Sources of such fetal cells include the placenta and umbilical cord tissue. A fetal-derived stromal matrix may possess "generic" tissue properties that may be further directed by the addition of growth factors or specific growth conditions. Fetal stromal cells can be inoculated onto the framework to form a "generic" living stromal matrix or tissue for culturing any of a variety of cells and tissues. However, in certain instances, it may be preferable to use a "specific" rather than "generic" stromal system, in which case stromal cells and elements can be obtained from a particular tissue, organ or individual. For example, stromal cells from hematopoietic tissue, including but not limited to fibroblasts, endothelial cells, macrophages/monocytes, adipocytes and reticular cells, can be used to form the three-dimensional stromal matrix for the long term culture of bone marrow in vitro. Similarly, stromal cells can be obtained from other specific tissues such as liver, pancreas, etc. for inoculation onto or into the matrix in the formation of a specific stromal matrix system. Furthermore, where the three-dimensional culture is to be used for ultimate implantation in vivo, it may be preferable to obtain the stromal cells and elements from the individual who is to receive the implant.

Once inoculated onto or into the three-dimensional framework, the stromal cells will proliferate on the framework, and elaborate growth factors, regulatory factors and extracellular matrix proteins that are deposited on the framework to form a living stromal matrix or tissue construct. Growth and regulatory factors can be added to the culture, but are not necessary since they are elaborated by the stromal support matrix. The three-dimensional system of this invention thus supports the maturation, differentiation, and segregation of cells in culture in vitro to form components of adult tissues analogous to counter parts found in vivo.

According to one embodiment, once the stromal cells have grown and proliferated on the framework to form the living stromal matrix, this tissue construct is subjected to standard conditions used for the cryopreservation of cells. Upon thawing of the cryopreserved cultures, the cells of the tissue construct are induced to express at least one gene that encodes a regulatory protein, such regulatory proteins including cytokines, growth factors, angiogenic factors, inflammatory mediators and/or stress proteins. The increased production of these factors in the matrix promotes the growth and development of the matrix itself (which can be used for the in vitro culture of stromal cells and/or ultimate implantation in vivo) as well as providing within the matrix factors that enhance the growth of cells that may be subsequently inoculated onto the matrix.

Thus, in an alternative embodiment, the living stromal matrix may itself be used as a supporting construct for the inoculation of tissue-specific parenchymal cells, e.g., liver, pancreas, bone marrow cells, for the in vitro culture and/or ultimate implantation in vivo of a tissue-specific three-dimensional construct as defined supra. According to this embodiment, the tissue-specific parenchymal cells can be inoculated onto the living stromal matrix after induction of the matrix by cryopreservation and subsequent thawing, in which case, the increased amounts of induced regulatory proteins in the matrix promotes the growth of the tissue-specific construct. Alternatively, the parenchymal cells may be inoculated onto the living stromal matrix prior to cryopreservation, i.e., the parenchymal cells are cultured on the stromal matrix (which has not been subjected to cryopreservation and thawing) and then the tissue-specific three-dimensional construct itself is cryopreserved as described herein and subsequently thawed, resulting in an increased amount of regulatory proteins such as growth factors and stress proteins for the enhanced growth of the construct. In yet an alternative embodiment, the stromal matrix is subjected to oxygen deprivation or nutrient deficiency, resulting in the induction of regulatory proteins such as growth factors or stress proteins. Parenchymal cells are then inoculated onto or into the matrix to form a tissue-specific three-dimensional tissue construct. The increased amounts of regulatory proteins in the matrix promotes the growth of the tissue-specific construct of the invention.

Induction of regulatory proteins as described herein occurs shortly after thawing and can last up to about 5 days or until the cells or tissues regain their normal metabolic state. Therefore, the cells or tissue constructs of this invention should be used or applied shortly after thawing.

Solely for ease of explanation, the detailed description of the invention is divided into the following sections: (1) establishment of the three-dimensional constructs of the invention (including the three-dimensional living stromal matrix and the tissue-specific three-dimensional construct); (2) cryopreservation and thawing of the constructs of the invention; and (3) induction of regulatory proteins in the constructs by cryopreservation and thawing.

5.1 Establishment of the Three-Dimensional Constructs of the Invention

The three-dimensional living stromal matrix, the three-dimensional tissue-specific construct, their maintenance, as well as various uses of these three-dimensional cultures are described in co-owned U.S. Pat. No. 4,963,489, which is incorporated herein by reference. Although the applicants are under no duty or obligation to explain the mechanism by which the invention works, a number of factors inherent in these three-dimensional culture systems may contribute to their success:

(a) The three-dimensional framework provides a greater surface area for protein attachment, and consequently, for the adherence of stromal cells.

(b) Because of the three-dimensionality of the framework, stromal cells continue to actively grow in contrast to cells in monolayer cultures, which grow to confluence, exhibit contact inhibition, and cease to grow and divide. The elaboration of growth and regulatory factors by replicating stromal cells may be partially responsible for stimulating proliferation and regulating differentiation of cells in culture.

(c) The three-dimensional framework allows for a spatial distribution of cellular elements which is more analogous to that found in the counterpart tissue in vivo.

(d) The increase in potential volume for cell growth in the three-dimensional system may allow the establishment of localized microenvironments analogous to native counterparts found in vivo.

(e) The three-dimensional matrix maximizes cell-cell interaction by allowing greater potential for movement of migratory cells, such as macrophages, monocytes and possibly lymphocytes in the adherent layer.

(f) It has been recognized that the maintenance of a differentiated cellular phenotype requires not only growth/differentiation factors but also the appropriate cellular interactions. The three-dimensional constructs of this invention effectively recreate the stromal tissue microenvironment.

The three-dimensional framework that forms the backbone of the living stromal matrix may be of any material and/or shape that allows cells to attach to it, or which can be modified or treated to allow cells to attach to it, and which allows cells to grow in more than one layer. A number of different materials may be used to form the support matrix, including, but not limited to, materials such as nylon (polyamides), DACRON (polyesters), polystyrene, polypropylene, polyacrylates, polyvinyl compounds (e.g., polyvinylchloride), polycarbonate (PVC), polytetrafluoroethylene (PTFE/TEFLON), THERMANOX (TPX), nitrocellulose, cotton, polyglycolic acid (PGA), polycaprolactones, collagen (in the form of sponges, braids, woven threads or contracted gels, etc.), catgut sutures, cellulose, gelatin, dextran, hydrogels, hyaluronic acid, tissue-derived materials (decellularized dermis), or other naturally occurring biodegradable or synthetic materials, including, for example, polyhydroxyalkanoates.

Any number of these materials may be woven into a mesh, for example, to form the three-dimensional framework or scaffold. Where the three-dimensional matrix is to be implanted in vivo, it is preferable, although not necessary, that the scaffold be biodegradable and thus it may be preferable to use biodegradable materials such as polyglycolic acid, polycaprolactones, cellulose, catgut suture material, gelatin or dextran. Where the cultures are to be maintained for long periods of time, non-degradable materials such as nylon, dacron, polystyrene, polyacrylates, polyvinyls, teflons, etc. may be preferred. Certain materials such as nylon or polystyrene may be poor substrates for cellular attachment and therefore, when these materials are used in the scaffold, it is preferable to pre-treat the scaffold prior to inoculation of the stromal cells to promote and optimize cell attachment. For example, nylon may be treated with 0.1 M acetic acid and incubated in polylysine, PBS, serum and/or collagen to coat the nylon. Polystyrene may be similarly treated using sulfuric acid.

Stromal cells comprising mesenchymal stem cells, prechondrogenic cells, fetal fibroblasts, undifferentiated stromal cells, chondrocytes, fibroblasts or fibroblast-like cells, or combinations thereof, with or without other cells and elements described below, are inoculated onto the matrix. As noted supra, these stromal cells may be derived from a variety of sources including organs, such as skin, cartilage, liver, pancreas, etc.

For example, fibroblasts may be readily isolated by disaggregation of an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes, either alone or in combination. These include but are not limited to trypsin, chymotrypsin, collagenase, elastase, and/or hyaluronidase, Dnase, pronase, dispase etc. The tissue may also be disrupted mechanically by the use of homogenizers, sonicators, blenders, pressure chambers, etc. For a review of tissue disaggregation techniques, see Freshney, *Culture of Animal Cells. A Manual of Basic Technique,* 2d Ed., A. R. Liss, Inc., New York, 1987, Ch. 9, pp. 107–126.

Once the tissue has been reduced to a suspension of individual cells, the suspension can be fractionated into subpopulations from which chondrocytes, fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, e.g., density gradient techniques, centrifugal elutriation (counter-streaming centrifugation), unit gravity separation, counter current distribution, electrophoresis and fluorescence-activated cell sorting. For a review of clonal selection and cell separation techniques, see Freshney, supra, Ch. 11 and 12, pp. 137–168.

For example, the isolation of fibroblasts can be carried out as follows: fresh tissue samples, e.g., skin, are thoroughly washed and minced in Hanks balanced salt solution (HBSS)

in order to remove serum. The minced tissue is incubated from 1–12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts cells can then be grown to confluency, lifted from the confluent culture and inoculated onto the three-dimensional framework (see, e.g., Naughton et al., 1987, J. Med. 18(3&4) :219–250). Fibroblast-like cells may also be isolated from human umbilical cords (33–44 weeks). Fresh tissues may be minced into pieces and washed with medium. The umbilical tissues may be disaggregated as described above. See also, Brittberg et al., 1994, New Eng. J. Med. 331 (No. 14):890–895 for the isolation of chondrocytes and see Wakitani et al., 1994, J. Bone and Joint Surg. 76-A (No. 4):579–592 for the isolation of chondrocyte progenitor cells.

Thus, using standard techniques, it is possible to isolate fibroblasts, mesenchymal stem cells, chondrocytes and other progenitor cell populations of a particular tissue. A particular cell type may then be inoculated onto the three-dimensional framework or scaffold by injecting, layering, dispersing, etc. the cells within, on, or throughout the framework structure. The cells are then cultured in conjunction with the framework under normal cell culture techniques that are well known in the art. Such culture techniques may employ the use of bioreactors to adjust the flow and pressurization of the chamber in which the cells are grown.

In addition to fibroblasts, or fibroblast-like cells, additional cells may be inoculated and/or co-cultured either with the fibroblasts or after removal of the fibroblasts. For example, such cells may include, but are not limited to, endothelial cells, pericytes, macrophages, monocytes, plasma cells, mast cells, adipocytes, etc. Where the fibroblasts-like cells are undifferentiated cells or progenitor cells, the addition of specific tissue cell types may induce differentiation of the fibroblast-like cells.

After inoculation of the framework support with stromal cells, the three-dimensional matrix is incubated in an appropriate nutrient medium. Such commercially available media includes RPMI-1640, Fisher's, Isocove's, McCoy's, and the like. It is important that the three-dimensional stromal matrix be suspended or floated in the medium during the inoculation period in order to maximize proliferative activity. In addition, the culture should be fed periodically to remove the spent medium, depopulate released cells, and add fresh medium.

Regardless of the shape of the framework, the openings of the framework should be of an appropriate size to allow the stromal cells to stretch across the openings. Maintaining actively growing stromal cells which stretch across the framework enhances the production of growth factors which are elaborated by the stromal cells, and thus enhances long term culture. In addition, the openings of the framework must allow for adequate diffusion of nutrients and waste products into and out of the structure and, in cases where implantation in vivo is desired, the openings must allow for vascularization at the site of implantation. For example, if the openings are too small, the stromal cells may rapidly achieve confluence but be unable to easily exit from the matrix; trapped cells may exhibit contact inhibition and cease production of the appropriate factors necessary to support proliferation. If the openings are too large, the stromal cells may be unable to stretch across the opening; this will also decrease stromal cell production of the appropriate factors necessary to support proliferation. When using a mesh type of framework, openings ranging from about 150 $\mu$m to about 220 $\mu$m are satisfactory. However, depending upon the three-dimensional structure and intricacy of the framework, other sizes may work equally well. In fact, any shape or structure that allows the stromal cells to stretch and continue to replicate and grow for lengthy time periods will work in accordance with the invention. For example, for felt-type frameworks, openings ranging from about 80 $\mu$m to about 120 $\mu$m are preferred.

During growth of the stromal cells on the matrix, the cells will proliferate and secrete tissue-specific extracellular matrix materials, e.g., connective tissue proteins. These extracellular matrix materials will coat the scaffold support material. In the case of a biodegradable scaffold or framework, the naturally secreted extracellular matrix materials will eventually replace the artificial support. Such naturally secreted extracellular matrix materials may be tissue-specific.

Once the three-dimensional stromal matrix has reached the appropriate degree of growth, tissue-specific cells (parenchymal cells) can be inoculated onto the stromal matrix to form a tissue-specific three-dimensional construct. The parenchymal or tissue-specific cells may be obtained by disaggregating the desired tissue using standard techniques as described supra. The entire cellular suspension can be used to inoculate the stromal matrix or particular cell types may be isolated from appropriate fractions of the cellular suspension as described supra. For a review of methods which may be utilized to obtain tissue-specific cells from various tissues, see, Freshney, supra, Chapter 20, pp. 257–288.

The cells chosen for inoculation will depend upon the tissue to be cultured. For example, when culturing skin, melanocytes and keratinocytes may be inoculated onto the stromal matrix. When culturing liver, hepatocytes may be inoculated onto the matrix. When culturing bone marrow, bone marrow cells are used as the inoculum and when culturing pancreas, pancreatic endocrine cells may be used. Other tissues to be cultured can include kidney, neurological tissue, and adrenal gland.

In the tissue-specific construct of this invention, extracellular matrix material that is organized and secreted by particular tissues containing stromal cells and parenchymal cells will be replicated in vitro. For example, and not by way of limitation, inoculation of keratinocytes on a confluent three-dimensional dermal fibroblast stromal matrix will result in the development of a basal membrane composed of collagen type IV between the dermal layer and the epidermal keratinocyte layer.

In fact, different proportions of the various types of collagen deposited on the stromal matrix prior to inoculation can affect the growth of the later-inoculated tissue-specific cells. For example, for optimal growth of hematopoietic cells, the matrix should preferably contain collagen types III, IV and I in an approximate ratio of 6:3:1 in the initial matrix. For three dimensional skin culture systems, collagen types I and III are preferably deposited in the initial matrix. The proportions of collagen types deposited can be manipulated or enhanced by selecting fibroblasts which elaborate the appropriate collagen type. This can be accomplished using monoclonal antibodies of an appropriate isotype or subclass that is capable of activating complement, and which define particular collagen types. These antibodies and complement can be used to negatively select the fibroblasts which express the desired collagen type. Alternatively, the stromal cells used to inoculate the matrix can be a mixture of cells which synthesize the appropriate collagen type desired. The distribution and origins of various types of collagen is shown in Table I.

TABLE I

DISTRIBUTIONS AND ORIGINS OF VARIOUS TYPES OF COLLAGEN

| Collagen Type | Principal Tissue Distribution | Cells of origin |
|---|---|---|
| I | Loose and dense ordinary connective tissue; collagen fibers | Fibroblasts and reticular cells; smooth muscle cells |
| | Fibrocartilage | |
| | Bone | Osteoblast |
| | Dentin | Odontoblasts |
| II | Hyaline and elastic cartilage | Chondrocytes |
| | Vitreous body of eye | Retinal cells |
| III | Loose connective tissue; reticular fibers | Fibroblasts and reticular cells |
| | Papillary layer of dermis | |
| | Blood vessels | Smooth muscle cells; endothelial cells |
| IV | Basement membranes | Epithelial and endothelial cells |
| | Lens capsule of eye | Lens fibers |
| V | Fetal membranes; placenta | Fibroblast |
| | Basement membranes | |
| | Bone | |
| | Smooth muscle | Smooth muscle cells |
| VI | Connective Tissue | Fibroblasts |
| VII | Epithelial basement membranes, anchoring fibrils | Fibroblasts, keratinocytes |
| VIII | Cornea | Corneal fibroblasts |
| IX | Cartilage | |
| X | Hypertrophic cartilage | |
| XI | Cartilage | |
| XII | Papillary dermis | Fibroblasts |
| XIV, undulin | Reticular dermis | Fibroblasts |
| XVII | P170 bullous pemphigoid antigen | Keratinocytes |

Thus, depending upon the tissue to be cultured and the site in vivo at which the living stromal tissue or tissue construct is to be placed, the appropriate stromal cell(s) may be selected to inoculate the three-dimensional matrix.

5.1.1. Genetically Engineered Constructs

In another embodiment, the three-dimensional constructs can act as vehicles for introducing genes and gene products in vivo, e.g., to promote the repair and/or regeneration of tissue defects, for wound healing or for use in gene therapies. For example, the stromal cells can be genetically engineered to express inflammatory mediators, such as IL-6, IL-8 and G-CSF, to promote wound healing. The cells could also or alternatively be genetically engineered to express, at a desired time, anti-inflammatory factors, e.g., anti-GM-CSF, anti-TNF, anti-IL-1, anti-IL-2, etc., to reduce the risk of rejection of an implanted tissue construct. Alternatively, the gene encoding the human complement regulatory protein, which prevents rejection of an implant by a host, may be inserted into human fibroblasts. McCurry et al., 1995, Nature Medicine 1:423–427.

In another embodiment, the stromal cells can be genetically engineered to express a gene which would exert a therapeutic effect, e.g., in the production of TGF-β to stimulate cartilage production, or other factors such as BMP-13 to promote chondrogenesis or stimulatory factors that promote migration of stromal cells and/or matrix deposition.

In addition, the stromal cells can be genetically engineered to express a gene for which a patient is deficient or to provide gene replacement therapy. For example, in cartilage defects, replacement or repaired cartilage may be designed specifically to meet the requirements of an individual patient; for example, the stromal cells may be genetically engineered to regulate one or more genes; or the regulation of gene expression may be transient or long-term; or the gene activity may be non-inducible or inducible.

The stromal cells can also be genetically engineered to "knock out" expression of factors that promote inflammation or rejection at the implant site. Negative modulatory techniques for the reduction of target gene expression levels or target gene product activity levels are discussed below. "Negative modulation", as used herein, refers to a reduction in the level and/or activity of target gene product relative to the level and/or activity of the target gene product in the absence of the modulatory treatment. The expression of a gene native to stromal cell can be reduced or knocked out using a number of techniques, for example, expression may be inhibited by inactivating the gene completely (commonly termed "knockout") using standard homologous recombination techniques. Usually, an exon encoding an important region of the protein (or an exon 5' to that region) is interrupted by a positive selectable marker (for example neo), preventing the production of normal mRNA from the target gene and resulting in inactivation of the gene. A gene may also be inactivated by creating a deletion or an inactivating insertion in part of a gene, or by deleting the entire gene. By using a construct with two regions of homology to the target gene that are far apart in the genome, the sequences intervening the two regions can be deleted. Mombaerts et al., 1991, Proc. Nat. Acad. Sci. U.S.A. 88:3084–3087. Alternatively, a gene may also be inactivated by deletion of upstream or downstream expression elements.

Antisense and ribozyme molecules which inhibit expression of the target gene can also be used in accordance with the invention to reduce the level of target gene activity. For example, antisense RNA molecules which inhibit the expression of major histocompatibility gene complexes (HLA) have been shown to be most versatile with respect to immune responses. Furthermore, appropriate ribozyme molecules can be designed as described, e.g., by Haseloff et al., 1988, Nature 334:585–591; Zaug et al., 1984, Science 224:574–578; and Zaug and Cech, 1986, Science 231:470–475. Still further, triple helix molecules can be utilized in reducing the level of target gene activity. These techniques are described in detail by L. G. Davis et al., eds, *Basic Methods in Molecular Biology,* 2nd ed., Appleton & Lange, Norwalk, Conn. 1994. Using any of the foregoing techniques, the expression of MHC class II molecules can be knocked out in order to reduce the risk of rejection of the tissue constructs described herein.

Methods that may be useful to genetically engineer the cells of the invention are well-known in the art and are further detailed in U.S. Pat. Nos. 4,963,489 and 5,785,964, the disclosures of which are incorporated herein by reference. For example, a recombinant DNA construct or vector containing an exogenous nucleic acid, e.g., encoding a gene product of interest, may be constructed and used to transform or transfect the stromal cells of the invention. Such transformed or transfected cells that carry the exogenous nucleic acid, and that are capable of expressing said nucleic acid, are selected and clonally expanded in the three-dimensional constructs of this invention.

Methods for preparing DNA constructs containing the gene of interest, for transforming or transfecting cells, and for selecting cells carrying and expressing the gene of interest are well-known in the art. See, for example, the techniques described in Maniatis et al., 1989, *Molecular Cloning, A Laboratory Manual,* Cold Spring Harbor Laboratory Press, Cold Spring Harbor, N.Y.; Ausubel et al., 1989, *Current Protocols in Molecular Biology,* Greene Publishing Associates & Wiley Interscience, N.Y.; and Sambrook et al., 1989, *Molecular Cloning: A Laboratory Manual,* 2nd Ed., Cold Spring Harbor Laboratory Press, Cold Spring Harbor, N.Y.

The cells can be engineered using any of a variety of vectors including, but not limited to, integrating viral vectors, e.g., retrovirus vector or adeno-associated viral vectors; or non-integrating replicating vectors, e.g., papilloma virus vectors, SV40 vectors, adenoviral vectors; or replication-defective viral vectors. Where transient expression is desired, non-integrating vectors and replication defective vectors may be preferred, since either inducible or constitutive promoters can be used in these systems to control expression of the gene of interest. Alternatively, integrating vectors can be used to obtain transient expression, provided the gene of interest is controlled by an inducible promoter. Other methods of introducing DNA into cells include the use of liposomes, lipofection, electroporation, a particle gun, or by direct DNA injection.

Host cells are preferably transformed or transfected with a nucleic acid, e.g., DNA, controlled by, i.e., in operative association with, one or more appropriate expression control elements such as promoter or enhancer sequences, transcription terminators, polyadenylation sites, among others, and a selectable marker. Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines which express the gene product.

Any promoter may be used to drive the expression of the inserted gene. For example, viral promoters include but are not limited to the CMV promoter/enhancer, SV40, papillomavirus, Epstein-Barr virus, elastin gene promoter and β-globin. Preferably, the control elements used to control expression of the gene of interest should allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary. Inducible promoters can be built into integrating and/or replicating vectors. For example, inducible promoters include, but are not limited to, metallothionien and heat shock protein.

According to one embodiment, the inducible promoters used for expressing exogenous genes of interest are those that are the native promoters of those regulatory proteins as disclosed herein that are induced as a result of cryopreservation and subsequent thawing. For example, the promoter of TGF-β, VEGF, or various known heat shock proteins can be used as the expression control element, i.e., can be operatively linked to an exogenous gene of interest in order to express a desired gene product in the tissue constructs of this invention, i.e., upon cryopreservation and subsequent thawing.

A variety of methods may be used to obtain the constitutive or transient expression of gene products engineered into the stromal cells. For example, the transkaryotic implantation technique described by Seldon et al., 1987, Science 236:714–718 can be used. "Transkaryotic", as used herein, suggests that the nuclei of the implanted cells have been altered by the addition of DNA sequences by stable or transient transfection. Preferably, the stromal cells are engineered to express such gene products transiently and/or under inducible control during the post-operative recovery period, or as a chimeric fusion protein anchored to the stromal cells, for example, as a chimeric molecule composed of an intracellular and/or transmembrane domain of a receptor or receptor-like molecule, fused to the gene product as the extracellular domain.

Furthermore, it may be desirable to prepare a construct having an extracellular matrix containing a foreign gene product, growth factor, regulatory factor, etc. This embodiment is based on the discovery that, during the growth of human stromal cells on a three-dimensional support framework, the cells synthesize and deposit on the framework a human extracellular matrix as produced in normal human tissue. The extracellular matrix is secreted locally by cells and not only binds cells and tissue together but also influences the development and behavior of the cells it contacts. The extracellular matrix contains various connective tissue proteins, e.g., fiber-forming proteins interwoven in a hydrated gel composed of a network of glycosaminoglycan chains. The glycosaminoglycans are a heterogeneous group of long, negatively charged polysaccharide chains, which (except for hyaluronic acid) are covalently linked to protein to form proteoglycan molecules. According to this embodiment of the invention, the stromal cells may be genetically engineered to express a desired gene product, or altered forms of a gene product, which will be present in the extracellular matrix having been laid down by the stromal cells.

The use of the genetically-engineered three-dimensional constructs of this invention has a number of advantages. First, since the constructs comprise eukaryotic cells, the gene product will be properly expressed and processed to form an active product. Second, the number of transfected cells can be substantially enhanced to be of clinical value, relevance, and utility. The three-dimensional constructs of the present invention allow for expansion of the number of transfected cells and amplification (via cell division) of transfected cells. Preferably, the expression control elements used should allow for the regulated expression of the gene so that the product can be over-synthesized in culture. The transcriptional promoter chosen, generally, and promoter elements specifically, depend, in part, upon the type of tissue and cells cultured. Cells and tissues which are capable of secreting proteins are preferable (e.g., those having abundant rough endoplasmic reticulum and golgi complex organelles). The over-produced gene product will then be secreted by the engineered stromal cell and may be incorporated into the extracellular matrix during cell growth and proliferation.

5.2. Cryopreservation and Thawing of the Constructs

Cryopreservation of the cells and tissues may be carried out according to known methods, such as those described in Doyle et al., supra. For example, but not by way of limitation, cells may be suspended in a "freeze medium" such as, for example, culture medium further comprising 15–20% FBS and 10% dimethylsulfoxide (DMSO), with or without 5–10% glycerol, at a density, for example, of about 4–10×10$^6$ cells/ml. The cells are dispensed into glass or plastic ampoules which are then sealed and transferred to the freezing chamber of a programmable freezer.

In the case of cryopreservation of tissues, the tissue may be grown in a multicavity bag or bioreactor in culture medium such as supplemented DMEM, the medium drained and replaced by a dimethylsulphoxide-based or other cryopreservative solution; for example, a solution of 10% (v/v) DMSO plus 10% (v/v) FBS in phosphate buffered saline (PBS) with calcium and magnesium can be used. The DMSO prevents ice crystal formation within the cells which can damage the cells. The FBS provides protective barriers against freezing damage to the cells. The PBS provides a balanced salt solution with ions essential for proper cell function and water transport during preservation. Individual bags or bioreactors are then frozen in a controlled rate freezer at the desired freezing temperature. Cryopreservative agents that can be used in the methods of this invention include, but are not limited to, DMSO, glycerol, ethylene glycol, or propylene glycol with added sucrose, sorbitol or trehalose, or combinations of these agents.

According to a preferred embodiment of the invention, the scaffold of the invention is placed within the cavity of multicavity bags and the bags are inoculated with stromal cells, e.g., fibroblasts, and rotated overnight to allow for even seeding of the stromal cells on the scaffold. During the following two weeks, the bags are fed statically with fresh DMEM medium (e.g., Life Technologies, Grand Island, N.Y.) at intervals of 2–7 days. The time at which the tissue constructs are ready for cryopreservation is determined by glucose consumption (see Section 6.1, infra). At that time, the tissue constructs are transferred through DMSO solutions of graded concentration to a final concentration of 10%.

The cells or tissues are cryopreserved or frozen to below −50° C.; more preferably, to below −65 to −70° C. However, the cells or tissues may be frozen to temperatures as low as −150 to −180° C. The optimal rate of freezing may be determined empirically, e.g., at a rate in the range of −0.1 to −5° C./min. For example, a freezing program that gives a change in temperature of −10° C./min through the heat of fusion may be used. Once the ampoules, bags or bioreactors have reached the desired cryopreservation temperature, they are transferred to a storage area, such as a constant temperature chest freezer or a liquid nitrogen tank.

According to one embodiment, tissue constructs are placed in a controlled rate freezer, in which the freezing rate is between about −0.1 to −2° C./min, as the construct is cooled from room temperature to −70° C. to −80° C. The construct can then be stored in a constant temperature chest freezer. The cryopreserved cells or tissues can be stored for a period of years, although they should be checked periodically for maintenance of viability.

The cells or tissues are prepared for use by rapid thawing followed by removal of the cryoprotective agent. According to a preferred embodiment, a maximum time of one minute is allowed from the time the cells or construct is taken from the storage freezer to its placement in a 34–37° C. water bath. The thawing time will vary depending upon the size of the sample (e.g., cells or tissue in cryoprotectant) and the volume of water used to thaw the sample. According to one embodiment, the cell sample or construct is allowed to thaw for approximately two minutes or until all ice has melted and then is immediately rinsed with room temperature 0.9% normal saline (NaCl) in order to remove the cryoprotectant. For example, a dermal tissue construct of the invention is generally rinsed four times (unagitated), a minimum of 5 seconds per rinse, in order to reduce the cryoprotectant concentration to below detectable levels.

After rinsing, the cells or construct can be submerged in saline for up to 30 minutes before use or application. If not being used within about 30 minutes, the thawed contents should be transferred under sterile conditions to a culture vessel containing appropriate medium. When cells are being thawed, it is advisable that the cells in the culture medium be adjusted to an initial density of about $3-6 \times 10^5$ cells/ml so that the cells can condition the medium as soon as possible, thereby preventing a protracted lag phase. In order to obtain the greatest benefit from the induction of regulatory proteins provided by this invention, thawing should be carried out shortly before application or use of the cells or tissue.

Figure 1:
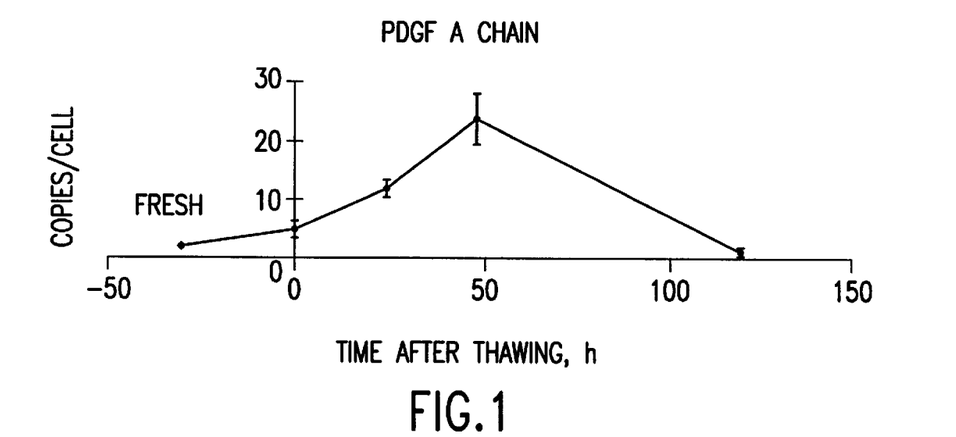
FIG. 1. Induction of PDGF A chain mRNA expression in three-dimensional dermal tissue constructs after cryopreservation and thawing relative to the level of mRNA expression for the same protein in fresh, i.e., non-cryopreserved, tissue constructs. Induction is expressed as a function of copies of mRNA/cell vs. time (in hours) after thawing. Error bars represent the standard errors of the means for triplicate measurements from three lots of cryopreserved constructs and one lot of fresh non-cryopreserved constructs.
Figure 2:
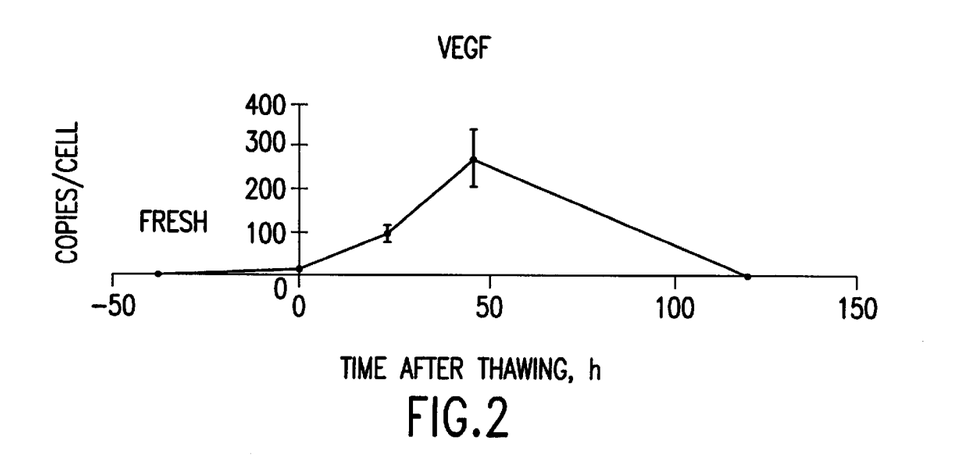
FIG. 2. Induction of VEGF mRNA expression in three-dimensional dermal tissue constructs after cryopreservation and thawing relative to the level of mRNA expression for the same protein in a fresh tissue construct. Induction is depicted as a function of copies of mRNA/cell versus time (in hours) after thawing. Error bars represent the standard errors of the means for triplicate measurements from three lots of cryopreserved constructs and one lot of fresh non-cryopreserved constructs.
Figure 3:
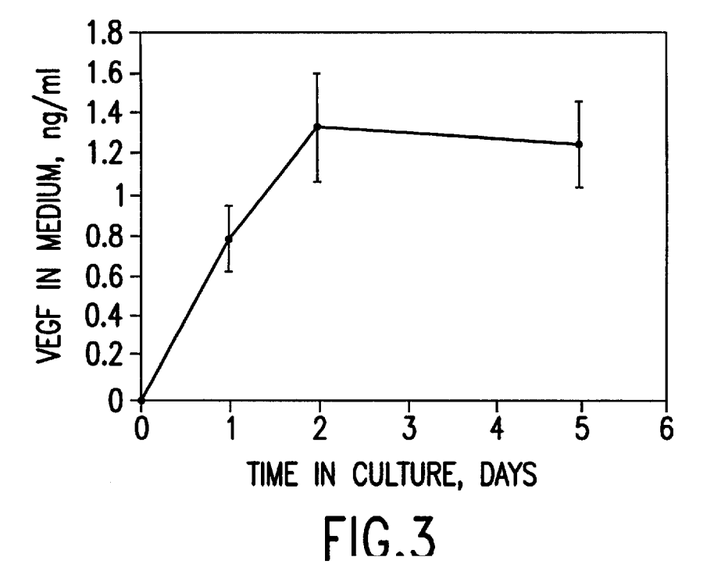
FIG. 3. Secretion of VEGF (in ng/ml) by three-dimensional dermal tissue constructs cryopreserved and thawed according to this invention. Error bars represent standard errors for quadruplicate measurements performed on 4 lots of dermal constructs. Secretion is depicted as a function of ng/ml amounts of VEGF versus time (i.e., days) in culture.
Figure 4:
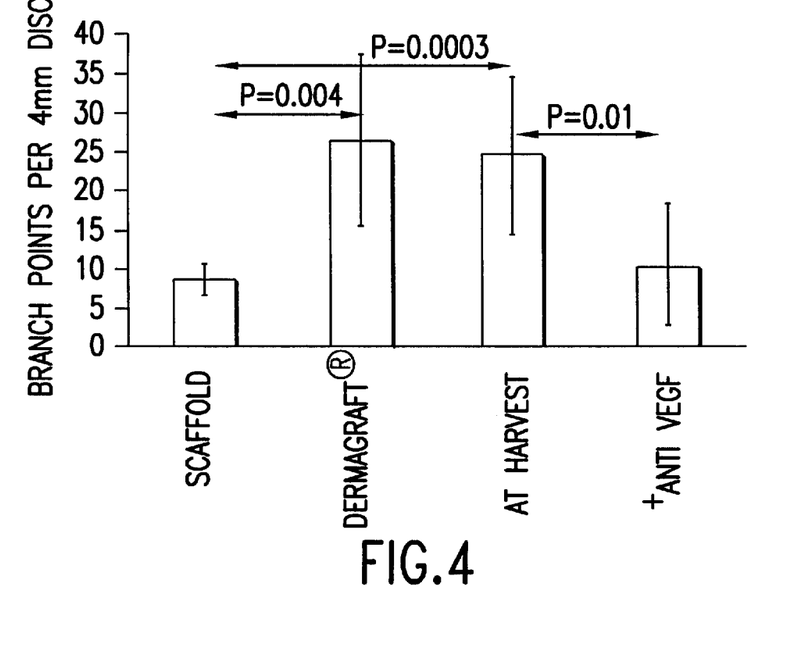
FIG. 4. Angiogenic activity displayed by dermal tissue constructs of the invention, i.e., after cryopreservation and thawing. The angiogenic activity of the constructs is compared to that of a non-cultured scaffold and is shown to be inhibited by an anti-VEGF neutralizing antibody.
Figure 5:
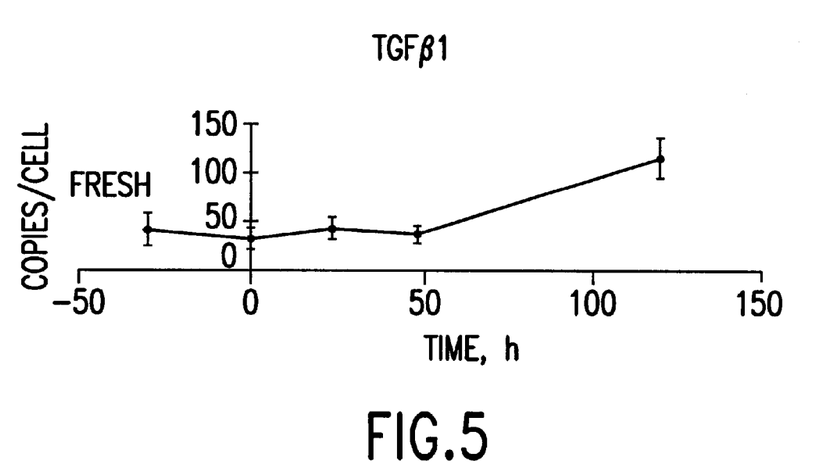
FIG. 5. Induction of TGF-β1 mRNA expression in three-dimensional dermal tissue constructs after cryopreservation and thawing relative to the level of mRNA expression for the same protein in a fresh tissue construct. Induction is expressed as a function of copies of protein/cell vs. time (in hours) after thawing. Error bars represent the standard errors of the means for triplicate measurements from three lots of cryopreserved constructs and one lot of fresh non-cryopreserved constructs.
Figure 6:
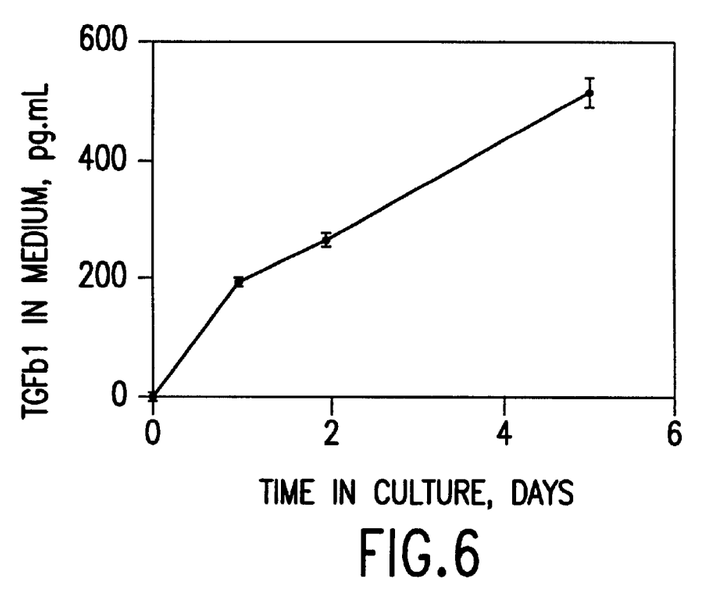
FIG. 6. Secretion of TGF-β1 by three-dimensional dermal constructs of the invention, i.e., after cryopreservation and thawing.
Figure 7:
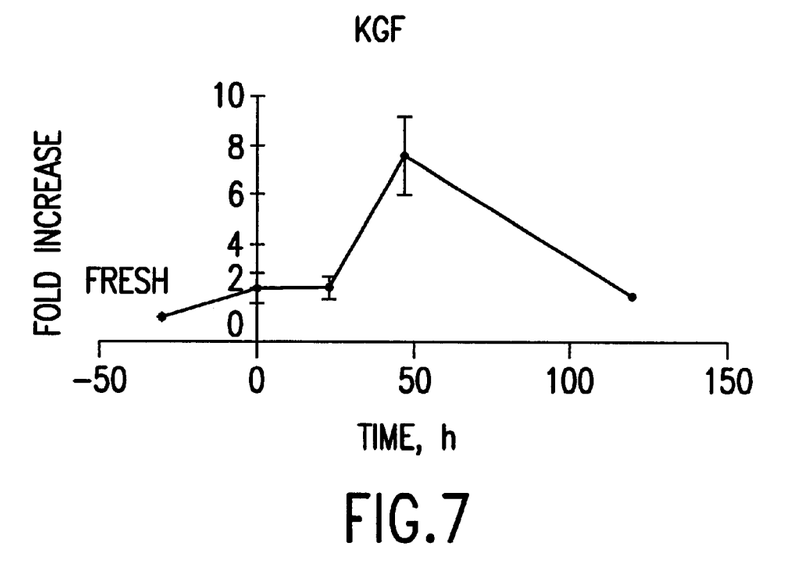
FIG. 7. Induction of KGF (keratinocyte growth factor) mRNA expression in three-dimensional dermal tissue constructs after cryopreservation and thawing relative to the level of mRNA expression for the same protein in fresh tissue constructs. Induction is depicted in terms of fold-increase of mRNA expression over non-cryopreserved constructs versus time (in hours) after thawing. Error bars represent the standard errors of the means for triplicate measurements from three lots of cryopreserved constructs and one lot of fresh non-cryopreserved constructs.
Figure 8:
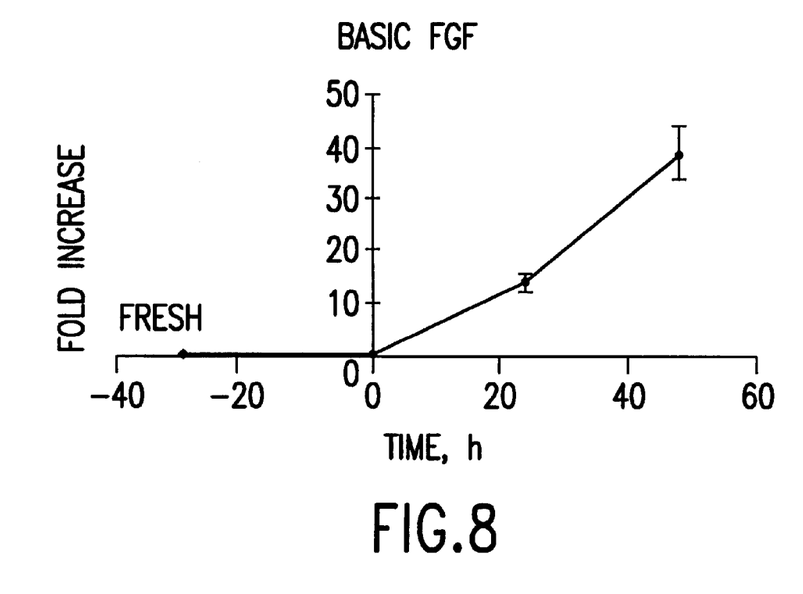
FIG. 8. Induction of bFGF mRNA expression in three-dimensional dermal tissue constructs after cryopreservation and thawing relative to the level of mRNA expression for the same protein in fresh tissue constructs. Induction is depicted in terms of fold-increase of mRNA expression over non-cryopreserved constructs versus time (in hours) after thawing. Error bars represent the standard errors of the means for triplicate measurements from three lots of cryopreserved constructs and one lot of fresh non-cryopreserved constructs.
Figure 9:
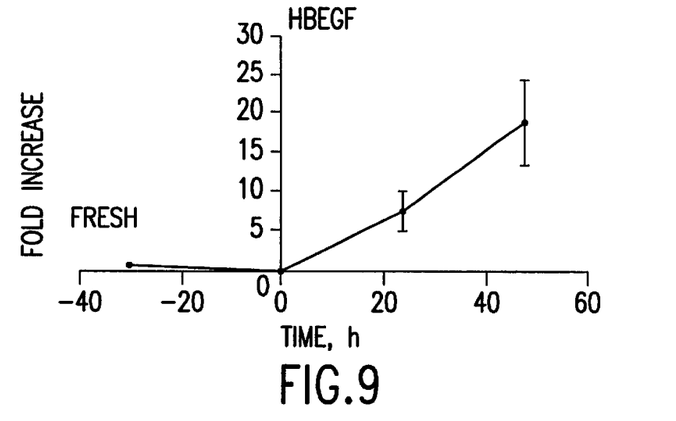
FIG. 9. Induction of HBEGF (heparin-binding epidermal growth factor) mRNA expression in three-dimensional dermal tissue constructs after cryopreservation and thawing relative to the level of mRNA expression for the same protein in fresh tissue constructs. Induction is depicted in terms of fold-increase of mRNA expression over non-cryopreserved constructs versus time (in hours) after thawing. Error bars represent the standard errors of the means for triplicate measurements from three lots of cryopreserved constructs and one lot of fresh non-cryopreserved constructs.
Figure 10:
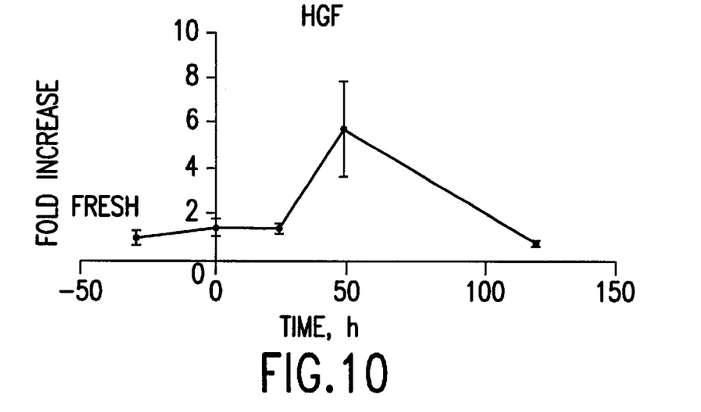
FIG. 10. Induction of HGF (hepatocyte growth factor) mRNA expression in three-dimensional dermal tissue constructs after cryopreservation and thawing relative to the level of mRNA expression for the same protein in fresh tissue constructs. Induction is depicted in terms of fold-increase of mRNA expression over non-cryopreserved constructs versus time (in hours) after thawing. Error bars represent the standard errors of the means for triplicate measurements from three lots of cryopreserved constructs and one lot of fresh non-cryopreserved constructs.
Figure 11:
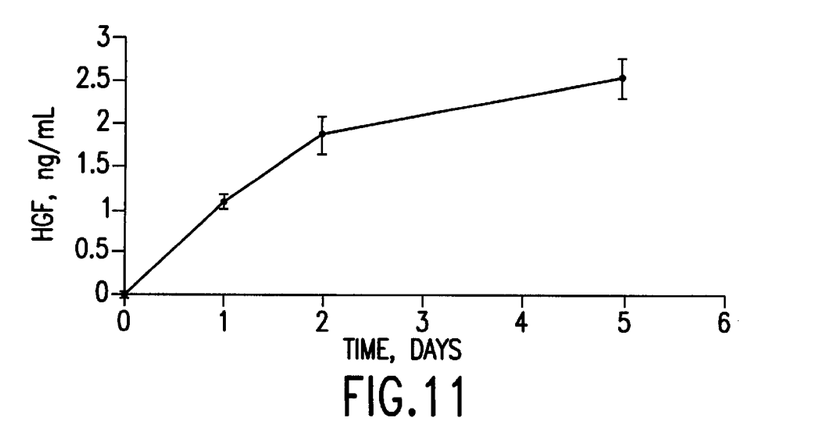
FIG. 11. Secretion of HGF by three-dimensional dermal constructs of the invention. Error bars represent standard errors of the means of values from 5 different lots of dermal constructs, each measured in duplicate. Secretion is depicted as a function of ng/ml amounts of HGF versus time (i.e., days) in culture after thawing.

5.3 Induction of Regulatory Proteins in the Constructs by Crypopreservation and Thawing After cryopreservation and thawing as described supra, the constructs of the invention possess an increased amount of regulatory proteins due to the induced expression of genes that encode those proteins. Examples of regulatory proteins induced according to this invention are VEGF, PDGF A chain, TGF-β1, HGF, KGF, HBEGF and basic FGF. The constructs therefore have elevated levels of mRNA encoding the regulatory proteins as well as elevated levels of the proteins themselves (see FIGS. 1–11 discussed infra).

The presence of elevated mRNA levels for the induced regulatory proteins can be determined using standard techniques in the art such as the quantitative reverse transcript Taqman polymerase chain reaction (QRTPCR) (see, e.g., Holland et al., 1991, Proc. Natl. Acad. Sci. USA 88: 7276–7280 and Lee, L. et al., 1993, Nucl. Acids Res. 21: 3761–3766). The presence of elevated protein levels for the induced regulatory proteins can also be determined by techniques known in the art such as standard ELISA assays and biological activity assays such as the chick chorioallantoic membrane (CAM) assay (see Section 6.3.1, infra).

5.4 Uses for the Constructs of the Invention

The compositions and methods described herein are useful for the treatment of wounds and other types of tissue damage. Wound healing is a complex process that involves several stages and is capable of sealing breaches to the integument in a controlled manner to form functionally competent tissue. The process begins with hemostasis followed by an inflammatory phase involving neutrophils and macrophages. The process continues with the development of granulation tissue and re-epithelialization to close the wound. Subsequently, scar tissue forms and is remodeled over the succeeding months to an approximation of the original anatomical structure. Each stage of the healing process is controlled by cellular interactions through regulatory proteins such as cytokines, growth factors, and inflammatory mediators as well as cell contact mechanisms. For example, inflammatory mediators such as IL-6, IL-8, and G-CSF induce lymphocyte differentiation and acute phase proteins, as well as neutrophil infiltration, maturation and activation, processes that are important in the inflammatory stages of wound healing. Other examples of regulatory proteins involved in the wound healing process are VEGF that induces angiogenesis during inflammation and granulation tissue formation, KGF that activates keratinocytes and TGF-β1 that induces deposition of extracellular matrix.

In chronic wounds, the healing process is interrupted at a point subsequent to hemostasis and prior to re-epithelialization, and is apparently unable to restart. Most of the inflammation seen in the wound bed is related to infection, but the inflammation gives rise to an environment rich in proteases that degrade regulatory proteins and thus interfere with the wound healing process. Similarly, in some medical conditions, such as diabetes, some of the regulatory proteins needed for wound healing are in short supply. For example, it has been found in a mouse model of non-insulin-dependent diabetes (e.g., the db/db mouse) that secretion of VEGF and PDGF and expression of the PDGF receptor are all depressed in wounds compared to the levels in wounds of normal mice.

Thus, the present invention allows the induction in the cells and constructs described herein of several regulatory proteins thought to be important in wound healing and which have been shown to be depleted in in vivo models of wound healing. Similarly, the induction provided by the present invention is also useful in the treatment of other types of tissue damage, e.g., traumatic or congenital, wherein the repair and/or regeneration of tissue defects or damage is desired. Thus, methods of the invention include methods for implanting the constructs of the invention in vivo, methods for promoting wound healing in vivo and methods for the repair or regeneration of tissue damage in vivo. In addition, the present compositions and methods are useful for enhancing the culture and/or differentiation of cells and tissues in vitro.

6. Example

Induction of Regulatory Proteins in Tissue Constructs of the Invention After Crypreservation and Thawing The subsections below describe the preparation, cryopreservation and thawing of a tissue construct of the invention and the induction of regulatory proteins in the construct upon cryopreservation and subsequent thawing.

6.1. Tissue Construct Preparation

According to one embodiment of this invention, a stromal matrix tissue construct as described herein was induced to express regulatory proteins after cryopreservation and thawing. The tissue construct was made by growing human dermal fibroblasts on a degradable three-dimensional scaffold; the construct containing a fibroblast density of 0.8–2 million cells $cm^{-2}$. The extracellular matrix of the construct contains collagen and proteoglycan in a structure resembling papillary dermis (DERMAGRAFT, Advanced Tissue Sciences, La Jolla Calif.).

More specifically, the scaffold was grown in ethylene vinyl acetate (EVA) multicavity bags containing 8 cavities, each of which carries one 2 inch by 3 inch piece of scaffold. The bags were inoculated with approximately $4.74 \times 10^6$ fibroblast cells in DMEM medium supplemented with 10% calf serum, glutamine, non-essential amino acids and ascorbate and rotated overnight at 37° C. to allow for even seeding of the stromal cells. The tissue cultures were fed statically with fresh medium at intervals of 2–7 days during the course of the next two weeks. Time for cryopreservation of the cultures was determined by glucose consumption using a Yellowsprings, Inc. Glucose Analyser and the cultures were harvested when just entering the stationary phase.

6.2 Crypopreservation and Thawing Procedure

During the cryopreservation procedure, the tissue constructs were transferred through a series of DMSO solutions of graded concentration to a final concentration of 10%, e.g., a solution of 10% (v/v) DMSO plus 10% (v/v) FBS in phosphate buffered saline (PBS) with calcium and magnesium. The cultures were then frozen in a controlled rate freezer over approximately 2 h, the temperature being reduced to the storage condition of −70° C. at a rate of about 0.2–0.4°/min. The cultures were maintained at this storage temperature for about 1–2 months.

The tissue constructs were then thawed for use by placing the bags containing the constructs in a 37° C. water bath. Thawing was carried out within 15 seconds from the time the constructs were taken out of the storage freezer. The bags were then opened and the tissue cultures rinsed 3 times with normal saline solution and then kept in a fourth saline rinse until use.

6.3 Induction of Regulatory Proteins 6.3.1. Methods and Materials

Upon thawing and removal of cryoprotectant, the tissue constructs were incubated in growth medium (DMEM containing 0.4% glucose and supplemented with 10% calf serum, non-essential amino acids, 2 mM L-glutamine and ascorbate) from 1 to 5 days without medium changes. Medium was harvested and the induction of various regulatory proteins was analyzed by ELISA using kits from R&D Systems (Minneapolis, Minn.) according to manufacturer's instructions.

In addition, a chick chorioallantoic membrane (CAM) assay was performed in order to measure angiogenic activity produced by the tissue constructs after cryopreservation and thawing. This assay is carried out by placing the tissue construct on an exposed chorioallantoic membrane of 10 day old fertile eggs and incubating the construct for 3 days at 37° C. Angiogenic activity is then determined by observing the development of blood vessels in the region underlying the tissue construct and counting new branch points in small blood vessels. Different angiogenic factors such as basic FGF and VEGF produce anatomically distinguishable angiogenic structures.

The presence in the tissue constructs of specific mRNA for regulatory proteins was estimated by quantitative RT-PCR using the ABI TaqMan method (Perkin-Elmer, Foster City, Calif.). RNA was isolated from the thawed tissue construct after incubation of the tissue in growth medium for various times up to 5 days after thawing, in order to allow the tissue to recover from the cryopreservation and thawing process. Total cellular RNA was extracted from the tissue using a rapid RNA Purification Kit (Amresco, Solon, OH or Ambion, Austin Tex.), precipitated with 2.5 volumes of ethanol and stored at −70° C. until used. The RNA (5 μg) was reverse transcribed using Superscript II murine Molony leukemia virus reverse transcriptase (Life Technologies, Gaitersburg, Md.) using random hexamer primers (Sigma, St. Louis, Mo.) as a large batch that was used for the amplification and estimation of multiple sequences. Samples of cDNA (generally equivalent to 200 ng total RNA) were amplified using the Taqman system, i.e., PCR primers and a probe modified with a fluorophore, 6-carboxyfluorescein, at the 5' end and a quencher, 6-carboxytetramethylrhodamine, at the 3' end specific for the mRNA in question. During polymerization, the 5' clearing function of the polymerase destroys the probe, separating the quencher from the fluorophore, resulting in fluorescence. The mRNA level is measured by the cycle time at which fluorescence rises above a threshold level. The method is calibrated using plasmids or DNA fragments containing the sequence of interest and the yield is determined by spiking extractions with known amounts of specific RNA sequences. Thus, amplification was detected in real time by the increase in fluorescein fluorescence observed and used to compare the content of the cDNA samples with a series of standards for the specific mRNA sequence. Linearized Bluescript plasmids containing the specific PCR product as an insert were used as standards. Measurements of the full range of the mRNA were performed on the same set of reverse transcripts from the same RNA preparations so that determinations would be comparable in terms of RNA extraction and reverse transcription. Loss of mRNA through the extraction and reverse transcriptase steps was determined by adding a known amount of full length synthetic mRNA for PDGF B chain, VEGF or TGF-β1 to the initial tissue extraction and estimating recovery by quantitative PCR.

Determination of mitogen-activated protein kinase (MAP) activation in fibroblast cells exposed to various stress/environmental stimuli was carried out as follows: ERK (Extracellular Receptor-activated Kinase), SAPK/JNK (Stress-Activated Protein Kinase/Jun Kinase) and p38 were estimated in 1% triton extracts of fibroblasts that had been exposed to various environmental stimuli using commercial kits for MAP kinase activity from New England Biolabs, Beverly, Mass. The MAP kinase was immunoprecipitated using a commercially available anti-MAP kinase antibody (New England Biolabs) and the precipitate was incubated with a specific artificial fusion protein substrate: Elk-1 for ERK, c-Jun for SAPK/JNK, and ATF-2 for p38 and ATP (New England Biolabs). The products were identified on Western blots using antibodies specific for the phosphorylated form of the substrate (New England Biolabs) and visualized by enzymatic chemiluminescence using the commercially available ECL kit Phototope (New England Biolabs).

6.3.2. Results

Results of these studies demonstrated that, after cryopreservation and thawing, there was a wide range of expression of various regulatory protein mRNAs, including PDGF A chain, VEGF, TGF-β1, bFGF, KGF, HGF and HBEGF, in the tissue constructs of the invention. For example, PDGF A chain mRNA was induced in the constructs from a concentration of about 2 copies/cell prior to cryopreservation, i.e., in fresh non-cryopreserved constructs, to 24 copies/cell at 48 h after cryopreservation and thawing. This was a maximal induction of 12-fold (see FIG. 1). VEGF mRNA was also induced in the constructs from a concentration of 6 copies/cell in fresh constructs to 272 copies/cell at 48 h after cryopreservation and thawing, followed by a decline to its original concentration by about 125 h. This represented a maximal induction of 48-fold (see FIG. 2).

The induction of TGF-β1 mRNA showed a different pattern than VEGF and PDGF A chain, remaining somewhat constant at about 42 copies/cell for the first two days after cryopreservation and thawing and then increasing to 111 copies/cell at day 5. This represented a 2.5-fold induction over the amount of TGF-β1 mRNA in fresh non-cryopreserved constructs (see FIG. 5).

Additional studies demonstrated that other regulatory protein mRNAs were also induced in the tissue constructs of the invention after cryopreservation and thawing. For example, KGF mRNA was induced in the cryopreserved and thawed constructs of the invention 7-fold at 48 h as compared to fresh non-cryopreserved constructs (see FIG. 7). bFGF and HBEGF mRNAs were also induced, 39-fold and 18-fold, respectively, at 48 h, although absolute amounts of mRNA seen were small (see FIGS. 8 and 9). HGF mRNA was induced 6-fold at 48 h (see FIG. 10).

In addition, ELISA analysis of conditioned medium of the cryopreserved and thawed tissue constructs of these studies demonstrated that the observed expression of regulatory protein mRNAs resulted in protein secretion. For example, the tissue constructs secreted physiologically relevant concentrations of VEGF (see FIG. 3). The VEGF secreted was further analyzed for angiogenic activity using the CAM assay described supra. As demonstrated in FIG. 4, the tissue constructs possessed striking angiogenic activity that was not shown by the control, i.e., a non-cultured scaffold alone. Furthermore, when the assay was carried out in the presence of an anti-VEGF neutralizing antibody (R&D Systems, Minneapolis Minn.), the angiogenic activity was reduced to control levels. These results indicate that the VEGF detected by ELISA and by expression of mRNA was functionally active and that the angiogenic activity of the tissue constructs was dependent on this VEGF.

TGF-β1 was also demonstrated by ELISA assay as being secreted by the tissue constructs of this invention. As demonstrated in FIG. 6, TGF-β1 was secreted into the culture medium continuously over the first 5 days in culture. bFGF was also secreted at about 50 pg/ml (data not shown) as was HGF, which was secreted by the constructs in physiologically significant amounts over 5 days in culture (see FIG. 11).

In yet another study, examination of two-dimensional gel electrophoretic analyses of proteins isolated from a dermal tissue construct after freezing and thawing demonstrated the induction of the stress protein HSP90 (see FIGS. 9A and 9B of provisional application 60/072,945, filed on Jan. 9, 1998, which has been incorporated by reference in int entirety). In a separate experiment, pieces of dermal tissue constructs, e.g., DERMAGRAFT, were incubated at various time points after cryopreservation and thawing, up to 4 h, with 20 $\mu$Ci/ml [$^{35}$S]-methionine. The tissue was extracted with 1% triton X-100 in the presence of protease and phosphatase inhibitors and the proteins separated by polyacrylamide gel electrophoresis (PAGE). Separation in the first (horizontal) dimension was by isoelectric focusing, i.e., by isoelectric point, and in the second dimension (vertical) by SDS-PAGE, i.e., by molecular weight. Both gels were loaded with the 5.28 $\mu$g of protein.

A comparison of the patterns of proteins expressed before cryopreservation (i.e., fresh constructs) versus 24 h after thawing (after cryopreservation) was carried out. Spots corresponding to many proteins were reduced in intensity in the cryopreserved and thawed constructs, while other proteins became more prominent. Certain well-established stress proteins were identified including HSP90 and GRP78. These two proteins represent members of two well-known groups of stress proteins that are generally not expressed together. Moreover, there were several quite prominent proteins that were induced by cryopreservation and thawing that have not been identified. The conclusion from this experiment was that a substantial number of proteins change expression as a result of cryopreservation and subsequent thawing and these include members of well-established families that are usually not induced together as well as other proteins.

In further analyzing the induction observed according to this invention, the induction of proteins associated with selected signal transduction pathways was examined. In particular, the proteins of the ERK, SAPK/JNK and p38-mitogen-associated protein kinase pathways were studied as described supra in Section 6.3.1. These proteins phosphorylate other proteins, frequently DNA binding proteins controlling gene expression, on serine or threonine residues, when activated by protein tyrosine kinases. ERK is mainly associated with growth factor receptor tyrosine kinase pathways whereas SAPK/JNK and p38 are associated with various cellular stress stimuli.

The activation of these proteins under various environmental stresses was compared to the activation observed following cryopreservation and thawing. ERK was strongly activated by EGF (a cytokine that uses a typical tyrosine kinase receptor), and was activated as well by azide (hypoxia), UV irradiation and high temperature (e.g., 42° C.). SAPK/JNK was activated by azide, UV, DMSO and glycerol while p38 was activated by EGF, azide, UV and glycerol.

Analysis of the activation of these proteins, over time, after cryopreservation and thawing indicated that no activation of the cellular stress-associated SAPK/JNK was observed over the course of 5 hours after thawing, but p38 was rapidly and dramatically induced, followed by rapid inactivation. At 2 hours after thawing ERK levels dropped to those seen in the control, i.e., fresh non-cryopreserved constructs. This pattern of activation and inactivation was both more intense and different from any seen following other stress stimuli.

As a result of these various studies, it was concluded that the variety of changes in protein synthesis seen in the tissue constructs of this invention after cryopreservation and thawing was unique and different from the changes seen after other environmental stresses.

6.4 Implantation of a Tissue Construct of the Invention at a Defect Site

According to one embodiment of the invention, a dermal tissue construct is implanted into the site of a wound or other tissue defect. The tissue construct has been previously cryopreserved and recently thawed and is rinsed in NaCl solution as described above. When ready to apply to the defect site, the NaCl solution is poured from the tissue construct and the tissue is placed into the defect site, as is, or is cut to fit into the defect site. The defect site is preferably surgically debrided, removing any necrotic or hyperkeratinized tissue. The defect site is also preferably cleaned/sterilized prior to implantation by scrubbing or rinsing with a sterilizing solution, e.g., iodine surgical scrub (e.g., 0.75% titratable iodine) or 0.9% sodium chloride solution, leaving a wound bed that meets the clinical criteria for skin grafting, i.e., a clean, granulating wound bed). After placement of the tissue in the site, the site is covered with a protective dressing or may be closed and sealed with sutures. The tissue construct should be left in the wound or defect site for at least, e.g., 1–2 days.

All patents, patent applications and publications cited above are incorporated herein by reference. The present invention is not to be limited in scope by the specific embodiments described which are intended as single illustrations of individual aspects of the invention. Functionally equivalent methods and compositions, in addition to those shown and described herein, will become apparent to those skilled in the art from the foregoing description and accompanying drawings. Such modifications are intended to fall within the scope of the appended claims.

What is claimed is:

1. A method for inducing the production of at least one regulatory protein selected from the group consisting of PDGF A, VEGF, TGF-β1, bFGF, KGFA, HGF and HBEGF, in cells in vitro comprising:
   (a) inoculating cells onto a substrate;
   (b) culturing the cells on the substrate; and
   (c) inducing the production of said at least one regulatory protein by subjecting the cells to cryopreservation and subsequent rapid thawing of between about 1 to about 3 minutes.

2. A method for inducing the production of at least one regulatory protein selected from the group consisting of PDGF A, VEGF, TGF-β1, bFGF, KGF, HGF and HBEGF, in a three-dimensional tissue construct in vitro comprising:
   (a) inoculating stromal cells onto a three-dimensional biocompatible, non-living framework;
   (b) culturing the cells in a nutrient environment to allow the cells to attach to and substantially envelop the framework to form a living stromal matrix on the framework thereby providing a three-dimensional tissue construct; and
   (c) inducing the production of said at least one regulatory protein by subjecting the construct to cryopreservation and subsequent rapid thawing of between about 1 to about 3 minutes.

3. The method of claim 1 or 2 in which the cells are transfected with an exogenous nucleic acid under the control of an expression control element.

4. The method of claim 3 in which the expression control element comprises an inducible promoter.

5. The method of claim 2, further comprising culturing parenchymal cells on the living stromal matrix, before or after induction of said regulatory protein.

6. The method of claim 1, 2 or 5 in which thawing is carried out in a water bath at approximately 34–37° C.

7. The method of claim 5 in which the parenchymal cells are keratinocytes, hepatic, kidney, pancreatic, neuronal, or intestinal cells.

8. The method of claim 2 or 5 in which the stromal cells are mesenchymal stem cells, fibroblast-like cells, fibroblasts, chondro-progenitor cells, chondrocytes or any combination thereof.

9. The method of claim 5 in which the parenchymal cells are transfected with an exogenous nucleic acid under the control of an expression control element.

10. The method of claim 5 in which the stromal cells are transfected with an exogenous nucleic acid under the control of an expression control element.

11. The method of claim 5 in which both the stromal and parenchymal cells are transfected with at least one exogenous nucleic acid under the control of an expression control element.

12. The method of claim 9, 10 or 11 in which the expression control element comprises an inducible promoter.

13. The method of claim 12 in which the promoter is from the gene encoding a TGF-β, VEGF, PDGF, KGF or basic FGF.

14. The method of claim 2 or 5 in which the framework is composed of a biodegradable material.

15. The method of claim 14 in which the biodegradable material is cotton, polyglycolic acid, a polycaprolactone, cat gut sutures, cellulose, gelatin, or dextran.

16. The method of claim 2 or 5 in which the framework is composed of a non-biodegradable material.

17. The method of claim 16 in which the non-biodegradable material is a polyamide, polyester, a polystyrene, a polypropylene, a polyacrylate, a polyvinyl, a polycarbonate, a polytetrafluoroethylene, or a nitrocellulose compound.

18. The method of claim 2 or 5 in which the framework is pre-coated with collagen.

19. The method of claim 2 or 5 in which the framework is a mesh.

20. A method for culturing parenchymal cells on a three-dimensional tissue construct prepared in vitro, wherein the tissue construct comprises a living stromal matrix comprising stromal cells and connective tissue proteins naturally secreted by the stromal cells attached to and substantially enveloping a framework composed of a biocompatible, non-living material formed into a three-dimensional structure, said tissue construct having been subjected to cryopreservation and subsequent rapid thawing of between about 1 to about 3 minutes and having an increased amount of at least one regulatory protein selected from the group consisting of PDGF A, VEGF, TGF-β1, bFGF, KGF, HGF and HBEGF, relative to constructs that are not subjected to said cryopreservation and subsequent rapid thawing; the method comprising:

(a) inoculating parenchymal cells onto the tissue construct; and (b) incubating the inoculated tissue construct in a nutrient environment so that the inoculated cells proliferate in culture.

21. A method for culturing parenchymal cells in vitro comprising:

(a) inoculating parenchymal cells onto a three-dimensional tissue construct prepared in vitro, wherein the tissue construct comprises a living stromal matrix comprising stromal cells and connective tissue proteins naturally secreted by the stromal cells attached to and substantially enveloping a framework composed of a biocompatible, non-living material formed into a three-dimensional structure, (b) subjecting the inoculated construct to cryopreservation and subsequent rapid thawing of between about 1 to about 3 minutes such that the inoculated construct contains an increased amount of at least one regulatory protein selected from the group consisting of PDGF A, VEGF, TGF-β1, bFGF, KGF, HGF and HBEGF, relative to inoculated constructs that are not subjected to said cryopreservation and subsequent thawing and (c) incubating the inoculated tissue construct in a nutrient environment so that the inoculated cells proliferate in culture.

* * * * *